United States Patent
Liu et al.

(10) Patent No.: US 10,632,111 B2
(45) Date of Patent: *Apr. 28, 2020

(54) DONEPEZIL DERIVATIVE AND USE THEREOF

(71) Applicant: NORATECH PHARMACEUTICALS, INC., Taipei (TW)

(72) Inventors: Fei Liu, Nanjing (CN); Cuixia Zhang, Nanjing (CN); Chenggang Lin, Nanjing (CN); Chunyan Zhou, Nanjing (CN); Pan Chen, Nanjing (CN); Wei Wang, Nanjing (CN); Lulu Wang, Nanjing (CN)

(73) Assignee: NANJING NORATECH PHARMACEUTICALS CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,500

(22) Filed: May 7, 2018

(65) Prior Publication Data

US 2018/0250278 A1    Sep. 6, 2018

Related U.S. Application Data

(63) Continuation of application No. 15/533,865, filed as application No. PCT/CN2015/095647 on Nov. 26, 2015, now Pat. No. 10,080,746.

(30) Foreign Application Priority Data

Dec. 11, 2014 (CN) .......................... 2014 1 0777222

(51) Int. Cl.
| | | |
|---|---|---|
| *A61K 31/445* | (2006.01) | |
| *C07D 211/22* | (2006.01) | |
| *A61K 47/26* | (2006.01) | |
| *A61K 47/18* | (2017.01) | |
| *A61K 9/19* | (2006.01) | |
| *A61K 9/08* | (2006.01) | |
| *A61K 31/045* | (2006.01) | |
| *A61K 31/235* | (2006.01) | |
| *A61K 47/44* | (2017.01) | |
| *A61K 9/00* | (2006.01) | |

(52) U.S. Cl.
CPC .............. *A61K 31/445* (2013.01); *A61K 9/08* (2013.01); *A61K 9/19* (2013.01); *A61K 31/045* (2013.01); *A61K 31/235* (2013.01); *A61K 47/183* (2013.01); *A61K 47/26* (2013.01); *A61K 47/44* (2013.01); *C07D 211/22* (2013.01); *A61K 9/0019* (2013.01)

(58) Field of Classification Search
CPC .. C07D 211/22; A61K 31/445; A61K 31/045; A61K 31/235; A61K 47/44
USPC .......................................................... 546/192
See application file for complete search history.

(56) References Cited

FOREIGN PATENT DOCUMENTS

| WO | WO 2007/052541 A1 | 5/2007 | |
|---|---|---|---|
| WO | WO-2007052541 A1 * | 5/2007 | ........... C07D 211/22 |
| WO | WO 2012/046062 A1 | 4/2012 | |

OTHER PUBLICATIONS

Lance Wilson et al , Benzyl Alcohol as an alternative Local Anesthetic (Year: 1999).*
International Search Report for PCT/CN2015/095647 dated Mar. 1, 2016.
Wilson et al., Annals of Emergency Medicine, Benzyl Alcohol as an Alternative Local Anesthetic, vol. 33, No. 5, May 1999, pp. 495-499.

* cited by examiner

*Primary Examiner* — Rita J Desai
(74) *Attorney, Agent, or Firm* — Birch, Stewart, Kolasch & Birch, LLP

(57) ABSTRACT

The present invention relates to a donepezil derivative of general formula (I) or a pharmaceutically acceptable salt thereof, wherein R in the formula is as disclosed herein; and a method for preparation thereof; and a composition comprising an effective amount of a compound of the general formula (I) or a pharmaceutically acceptable salt thereof. The present invention also relates to use of a compound of the general formula (I) or a pharmaceutically acceptable salt thereof in preparing a medicament for treating a disease resulted from an abnormality in acetylcholinesterase activity.

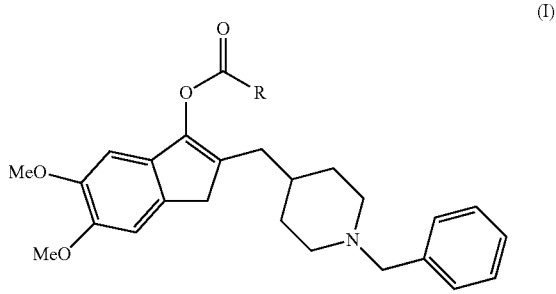

14 Claims, 3 Drawing Sheets

DONEPEZIL DERIVATIVE AND USE THEREOF

This application is a Continuation of copending application Ser. No. 15/533,865 filed on Jun. 7, 2017, which is the U.S. National Phase of PCT/CN2015/095647, filed Nov. 26, 2015, and which claims priority to Application No. 2014-10777222.4 filed in China on Dec. 11, 2014, the entire contents of all of which are expressly incorporated by reference into the present application.

FIELD OF THE INVENTION

The present invention relates to the field of pharmaceutical chemistry, and specifically relates to a donepezil derivative of general formula (I) or a pharmaceutically acceptable salt thereof, and use of such compounds in preparing a medicament for treating a disease resulted from an abnormality in acetylcholinesterase activity.

BACKGROUND OF THE INVENTION

In recent years, accompanying the phenomenon of population aging, the prevalence of Alzheimer's disease (AD) with dementia as the main symptom is getting higher. AD patients have poor memory, and there are often cases of forgetting to take medicine or taking wrong medicine. Some AD patients often do not admit that they are sick, and refuse to take medicine. Therefore, there is an urgent need for a long acting medicament for treating AD which is able to reduce the number of medication and improve patient compliance.

Donepezil, being an acetylcholinesterase inhibitor, is useful in treating Alzheimer's disease (AD). It has the advantages of high efficacy, easier absorption and lower toxicity. However, after administration, the rapid increase of drug concentration in blood may lead to adverse effects such as vomiting, diarrhea or insomnia.

In order to solve the above-mentioned problems, the present invention provides a class of novel compounds.

BRIEF SUMMARY OF THE INVENTION

An objective of the present invention is to provide a donepezil derivative or a pharmaceutically acceptable salt thereof. Another objective of the present invention is to provide a method for preparing a donepezil derivative or a pharmaceutically acceptable salt thereof. A further objective of the present invention is to provide use of such compounds in preparing a medicament for treating a disease resulted from an abnormality in acetylcholinesterase activity.

The objectives of the present invention are achieved by the following technical solutions. The present invention relates to a donepezil derivative of general formula (I) or a pharmaceutically acceptable salt thereof

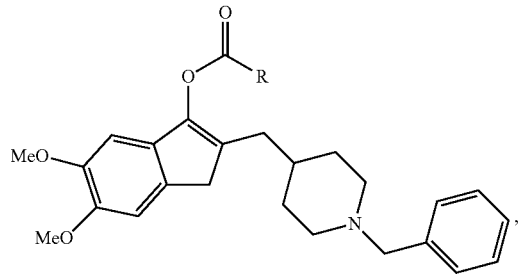

(I)

wherein R is a $C_{5-17}$ alkyl group.

According to the present invention, in the donepezil derivative of general formula (I) or a pharmaceutically acceptable salt thereof, R is preferably an n-pentane, an n-hexane, an n-heptane, an n-octane, an n-nonane, an n-decane, an n-undecane, an n-tridecan, an n-pentadecane, or an n-heptadecane, more preferably an n-pentane, an n-hexane, an n-heptane, an n-octane, an n-nonane, or an n-decane, and most preferably an n-hexane, an n-heptane, an n-octane, or an n-nonane.

According to the present invention, the donepezil derivative of general formula (I) or a pharmaceutically acceptable salt thereof preferably includes:

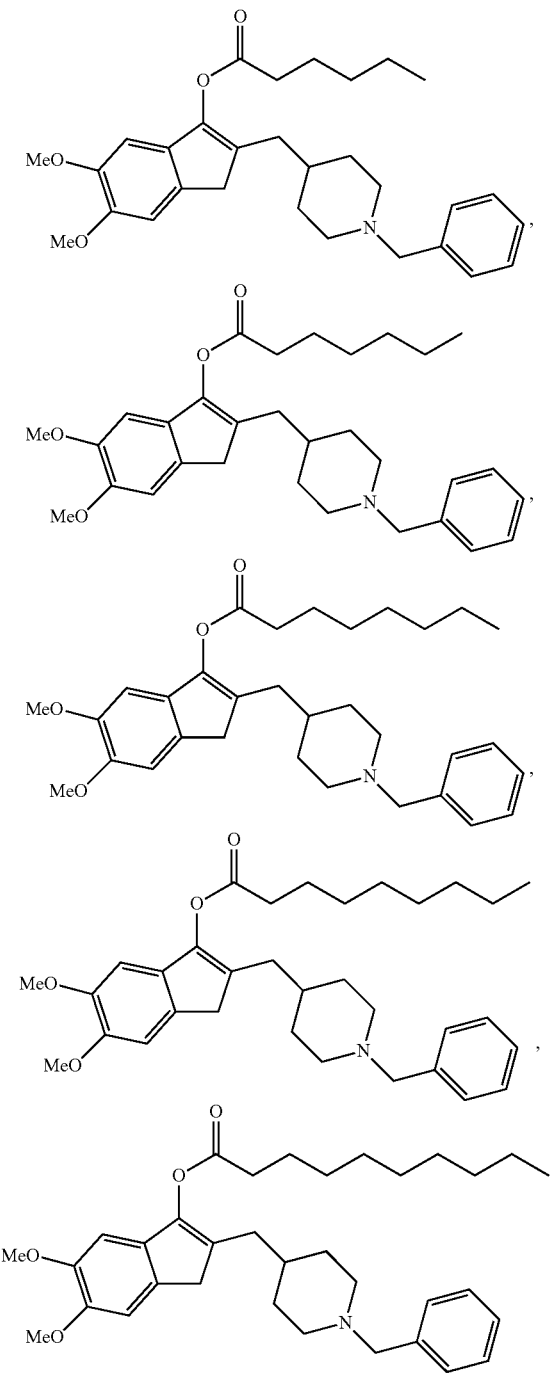

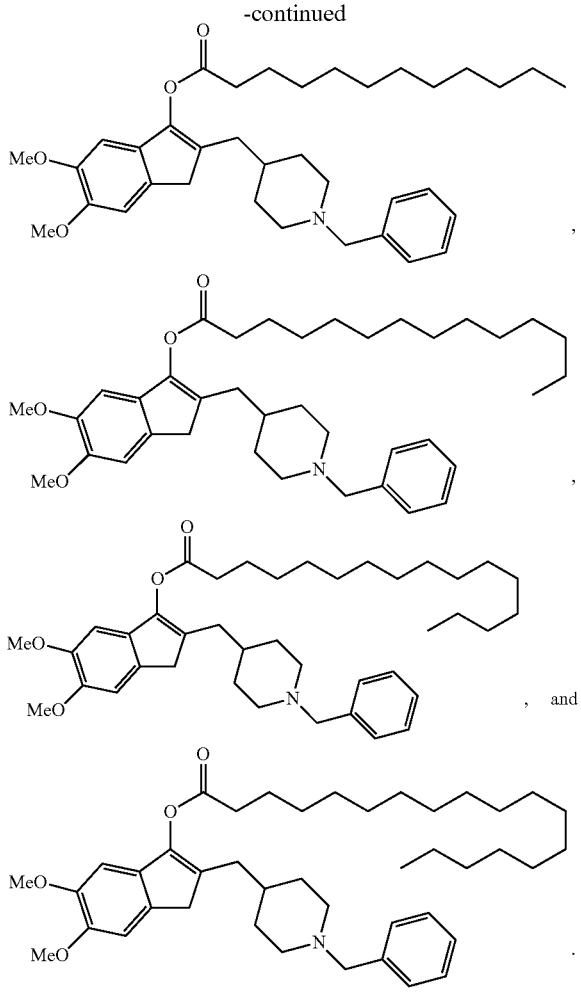

,

,

, and

.

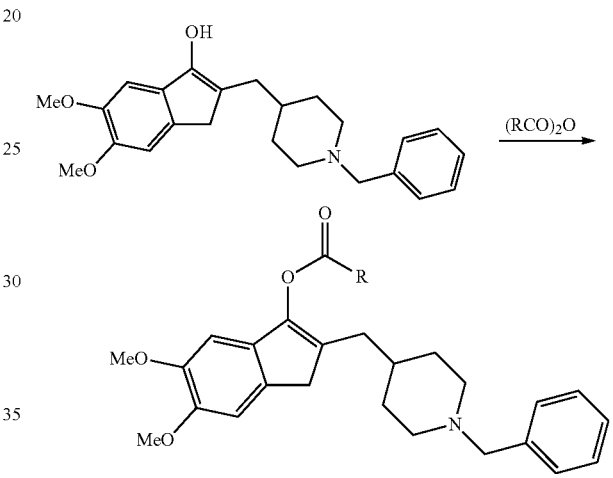

The present invention also provides use of a compound of the present invention or a pharmaceutically acceptable salt thereof in preparing a medicament for treating a disease resulted from an abnormality in acetylcholinesterase activity. Said disease includes Alzheimer's disease.

In the present invention, unless otherwise specified, the meanings of the terms used are as follows.

The denotation of the number of carbon atoms in a group, for example, $C_{1-10}$, means that the group may contain 1 carbon atom, 2 carbon atoms, 3 carbon atoms, . . . , and up to 10 carbon atoms. The term "or" may be used interchangeably with the term "and/or", unless otherwise clearly dictated in the context.

Alkyl group refers to a saturated aliphatic hydrocarbon group with said carbon atoms, including linear and branched hydrocarbon groups. Alkyl group includes but is not limited to methyl group, ethyl group, propyl group, isopropyl group, n-butyl group, isobutyl group, tert-butyl group, n-pentyl group, n-hexyl group, etc.

Pharmaceutically acceptable salts refer to the salts that retain the bioavailability and properties of the parent compound, acid salts are obtained through the reaction of the free base of the parent compound with an inorganic acid or an organic acid. The inorganic acid includes but is not limited to hydrochloric acid, phosphoric acid, and sulfuric acid. The organic acid includes but is not limited to acetic acid, trichloroacetic acid, dichloroacetic acid, propionic acid, butyric acid, maleic acid and p-toluenesulfonic acid.

The present invention further provides a pharmaceutical composition, comprising a compound of the present invention as mentioned above or a pharmaceutically acceptable salt thereof, and a pharmaceutically acceptable excipient.

The excipient refers to an inert substance that is added to the pharmaceutical composition to further facilitate the administration of the compound. Examples of the excipient include (but are not limited to) a castor oil, a soybean oil, a sesame oil, an *arachis* oil, a corn oil, a cottonseed oil, and glycerides. The excipient is preferably a castor oil.

Examples of a hydrotropic agent include (but are not limited to) a benzyl benzoate and alcohols. The hydrotropic agent is preferably a benzyl benzoate.

Examples of a pain relief agent include (but are not limited to) benzyl alcohol.

The compound of the present invention is prepared by the following process.

R is a $C_{5-17}$ alkyl group.

The donepezil used in preparing the compounds of the present invention is commercially available, or may be prepared according to known processes.

The compounds of the present invention were tested for pharmacokinetics in SD rats. The results demonstrate that the compounds of the present invention have the advantages of long half-life and avoiding rapid increase of plasma drug concentration.

DETAILED DESCRIPTION OF THE INVENTION

Figure 1:
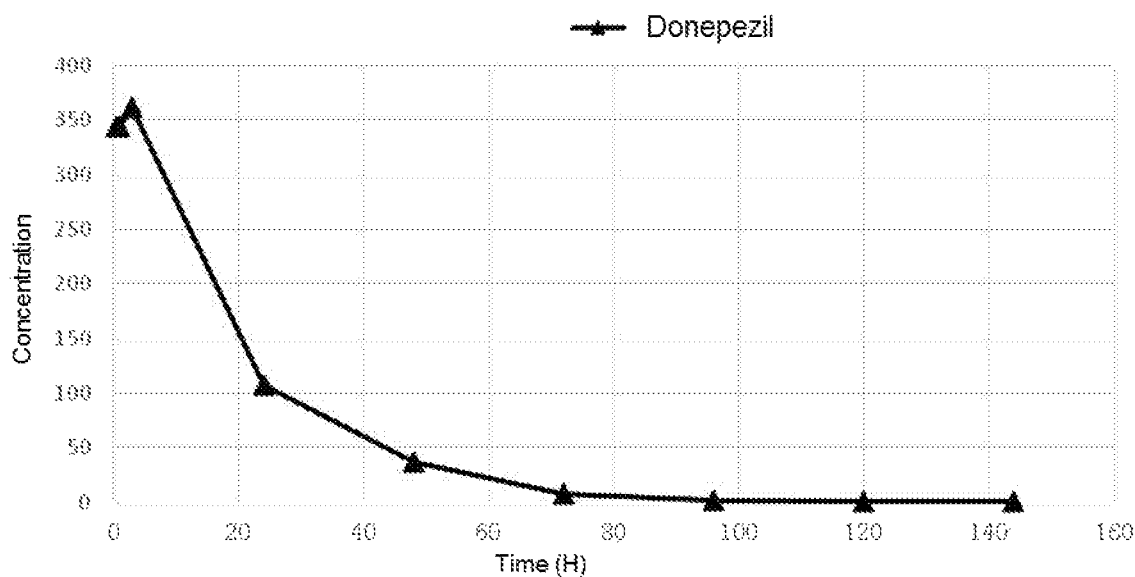
FIG. 1 shows the relationship between drug concentration in plasma and time in the group of rats administered with donepezil.

In order to describe the present invention in more detail, the following preparation examples are given. However, the scope of the present invention is not limited thereto.

Example 1

Compound 1: Preparation of Donepezil Acetate

Donepezil (50.0 g, 132 mmol) was added to a 2,000 ml three-neck round-bottom flask (equipped with an argon protection, a thermometer, a mechanical stirrer, and a constant pressure dropping funnel), the air was replaced with nitrogen, and 600 ml of anhydrous tetrahydrofuran was added and stirred to dissolve. Then cool the system temperature to −60 to −78° C. Lithium bis(trimethylsilyl)amide (200 ml, 1.0 mol/L, 200 mmol) was added to a constant pressure dropping funnel through a double-ended needle rapidly at once time. After stirring at −60 to −78° C. for 15 to 30 minutes, the temperature was naturally raised to 0 to 10° C. The system temperature was then lowered to −60 to −78° C. Acetic anhydride (20.4 g, 200 mmol) was dissolved in 200 ml of anhydrous tetrahydrofuran and added to a constant pressure dropping funnel rapidly at once time. After stirring at −60 to −78° C. for 30 minutes, the temperature was naturally raised to room temperature (20~30° C.). Examine complete reaction by TLC. The reaction system was placed in an iced water bath and 250 ml of saturated ammonium chloride solution was added dropwise. After completing the dropwise addition, the mixture was transferred to a separatory funnel and removal of the aqueous layer, and then wash once with 250 ml of 20% sodium chloride solution. Wash with 250 ml of saturated sodium chloride solution and then the mixture was transferred to a separatory funnel and removal of the aqueous layer. The organic phase was dried by anhydrous sodium sulfate and the solvent is removed under reduced pressure. Crystallization was done by using 500 ml of isopropanol, and 41 g of a white solid (yield: 73.7%) was obtained. HPLC (aera): 95.71%.

Mass spectrum (m/z): $[M+H]^+$=422.3.

$^1$H-NMR(CDCl$_3$) δ: 7.33-7.29 (4H, d), 7.25-7.27 (1H, m), 6.99 (1H, s), 6.62 (1H, s), 3.90 (3H, s), 3.90 (3H, s), 3.50 (2H, s), 3.27 (2H, s), 2.88-2.91 (2H, d), 2.36 (3H, s), 2.29-2.31 (2H, d), 1.92-1.97 (2H, t), 1.66-1.69 (2H, d), 1.51-1.52 (1H, m), 1.29-1.35 (2H, m).

Example 2

Compound 2: Preparation of Donepezil Hexanoate

Donepezil (25.0 g, 65.9 mmol) was added to an 1,000 ml three-neck round-bottom flask (equipped with an argon protection, a thermometer, a mechanical stirrer, and a constant pressure dropping funnel), the air was replaced with nitrogen, and 300 ml of anhydrous tetrahydrofuran was added and stirred to dissolve. Then the system temperature was cooled to −60 to −78° C. Lithium bis(trimethylsilyl) amide (100 ml, 1.0 mol/L, 100 mmol) was added to a constant pressure dropping funnel through a double-ended needle rapidly at once time. After stirring at −60 to −78° C. for 15 to 30 minutes, the temperature was naturally raised to 0 to 10° C. The system temperature was then lowered to −60 to −78° C. Then caproic anhydride (21.4 g, 100 mmol) was dissolved in 100 ml of anhydrous tetrahydrofuran and added to a constant pressure dropping funnel rapidly at once time. After stirring at −60 to −78° C. for 30 minutes, the temperature was naturally raised to room temperature (20-30° C.). Examine complete reaction by TLC. The reaction system was placed in an iced water bath and 250 ml of saturated ammonium chloride solution was added dropwise. After completing the dropwise addition, the mixture was transferred to a separatory funnel and removal of the aqueous layer, and then wash once with 250 ml of 20% sodium chloride solution. Wash with 250 ml of saturated sodium chloride solution and then the mixture was transferred to a separatory funnel and removal of the aqueous layer. The organic phase was dried by anhydrous sodium sulfate and the solvent was removed under reduced pressure. 29.3 g of oily substance was obtained (yield: 93%). Insolubles were removed from the oily substance by heating and dissolving in 225 ml of n-heptane and then filtrating. Subsequently, 22.5 ml of ethanol was added and subjected to cooling crystallization. Keep temperature under −5 to −10° C. for 1 hour and then perform filtration. Wash with 50 ml of cold n-heptane/ethanol (10:1) and drain. Perform vacuum drying to obtain 21.0 g of grey solid (yield: 66.7%), with HPLC (aera): 99.08%.

Mass spectra (m/z): $[M+H]^+$=478.4.

$^1$H-NMR(CDCl$_3$) δ:7.32-7.31 (4H, d), 7.25-7.27 (1H, m), 6.98 (1H, s), 6.60 (1H, s), 3.89 (6H, s), 3.49 (2H, s), 3.26 (2H, s), 2.86-2.89 (2H, d), 2.60-2.64 (2H, t), 2.28-2.29 (2H, d), 1.91-1.93 (2H, t), 1.81-1.84 (2H, t), 1.65-1.68 (2H, t), 1.20-1.60 (7H, m), 0.95-0.97 (3H, t).

Example 3

Compound 3: Preparation of Donepezil Heptanoate

The preparation process was the same as that of Example 2. Donepezil (40.0 g, 105.4 mmol) was reacted with heptanoic anhydride (38.82 g, 242.4 mmol) to obtain 42.30 g of donepezil heptanoate (yield: 81.7%) with HPLC (aera): 98.2%.

Mass spectrum (m/z): $[M+H]^+$=492.4.

$^1$H-NMR(CDCl$_3$) δ:7.32-7.31 (4H, d), 7.26-7.27 (1H, m), 6.98 (1H, s), 6.59 (1H, s), 3.89 (3H, s), 3.90 (3H, s), 3.50 (2H, s), 3.26 (2H, s), 2.87-2.89 (2H, d), 2.60-2.64 (2H, t), 2.27-2.29 (2H, d), 1.90-1.93 (2H, t), 1.80-1.83 (2H, t), 1.65-1.68 (2H, t), 1.20-1.60 (9H, m), 0.90-0.96 (3H, t).

Example 4

Compound 4: Preparation of Donepezil Octanoate

The preparation process was the same as that of Example 2. Donepezil (46.16 g, 121.6 mmol) was reacted with octanoic anhydride (38.82 g, 242.4 mmol) to obtain 46.0 g of donepezil octanoate (yield: 74.8%) with HPLC (aera): 98.2%.

Mass spectrum (m/z): $[M+H]^+$=506.4.

$^1$H-NMR(CDCl$_3$) δ:7.32-7.31 (4H, d), 7.26-7.27 (1H, m), 6.98 (1H, s), 6.59 (1H, s), 3.89 (3H, s), 3.90 (3H, s), 3.49 (2H, s), 3.26 (2H, s), 2.86-2.89 (2H, d), 2.60-2.63 (2H, t), 2.27-2.29 (2H, d), 1.90-1.96 (2H, t), 1.80-1.83 (2H, t), 1.65-1.68 (2H, t), 1.10-1.60 (11H, m), 0.90-0.96 (3H, t).

Example 5

Compound 5: Preparation of Donepezil Nonanoate

The preparation process was the same as that of Example 2. Donepezil (19.0 g, 50.1 mmol) was reacted with nonanoic anhydride (22.7 g, 76.2 mmol), and subjected to post-processing. Insolubles were removed by filtration before crystallization, and the crystallization temperature was −15 to −20° C. 17.8 g of the compound donepezil nonanoate was obtained (yield: 68.3%) with HPLC (area): 98.15%.

Mass spectrum (m/z): [M+H]$^+$=520.4.

$^1$H-NMR(CDCl) δ:7.32-7.31 (4H, d), 7.25-7.26 (1H, m), 6.98 (1H, s), 6.59 (1H, s), 3.896 (3H, s), 3.889 (3H, s), 3.49 (2H, s), 3.26 (2H, s), 2.86-2.89 (2H, d), 2.60-2.63 (2H, t), 2.27-2.29 (2H, d), 1.91-1.96 (2H, t), 1.81-1.85 (2H, t), 1.65-1.68 (2H, t), 1.18-1.65 (13H, m), 0.88-0.91 (3H, t).

Example 6

Compound 6: Preparation of Donepezil Decanoate

The preparation process was the same as that of Example 2. Donepezil (25.0 g, 65.9 mmol) was reacted with decanoic anhydride (32.6 g, 100 mmol), and subjected to post-processing. Insolubles were removed by filtration before crystallization. 21.9 g of the compound donepezil decanoate was obtained (yield: 62.2%) with HPLC (area): 98.15%.

Mass spectrum (m/z): [M+H]$^+$=534.4.

$^1$H-NMR(CDCl$_3$) δ:7.32-7.31 (4H, d), 7.26-7.28 (1H, m), 6.98 (1H, s), 6.59 (1H, s), 3.891 (3H, s), 3.899 (3H, s), 3.49 (2H, s), 3.26 (2H, s), 2.86-2.89 (2H, d), 2.60-2.63 (2H, t), 2.27-2.29 (2H, d), 1.90-1.94 (2H, t), 1.80-1.83 (2H, t), 1.65-1.68 (2H, t), 1.30-1.62 (15H, m), 0.89-0.93 (3H, t).

Example 7

Compound 7: Preparation of Donepezil Dodecanoate

The preparation process was the same as that of Example 2. Donepezil (15.0 g, 39.5 mmol) was reacted with dodecanoic anhydride (23.0 g, 60.0 mmol), and subjected to post-processing. Insolubles were removed by filtration before crystallization. 14.3 g of the compound donepezil dodecanoate was obtained (yield: 64.4%) with HPLC (area): 98.15%.

Mass spectrum (m/z): [M+H]$^+$=562.4.

$^1$H-NMR(CDCl3) δ:7.32-7.30 (4H, d), 7.26-7.27 (1H, m), 6.98 (1H, s), 6.59 (1H, s), 3.890 (3H, s), 3.899 (3H, s), 3.50 (2H, s), 3.26 (2H, s), 2.87-2.90 (2H, d), 2.59-2.63 (2H, t), 2.27-2.29 (2H, d), 1.91-1.97 (2H, t), 1.79-1.83 (2H, t), 1.65-1.68 (2H, t), 1.28-1.49 (19H, m), 0.90-0.92 (3H, t).

Example 8

Compound 8: Preparation of Donepezil Tetradecanoate

The preparation process was the same as that of Example 2. Donepezil (2.00 g, 5.27 mmol) was reacted with tetradecanoaic anhydride (3.5 g, 8.00 mmol), and subjected to post-processing. Insolubles were removed by filtration before crystallization. 1.93 g of the compound donepezil tetradecanoate was obtained (yield: 62.0%) with HPLC (area): 98.15%.

Mass spectrum (m/z): [M+H]$^+$=590.5.

$^1$H-NMR(CDCl3) δ:7.32-7.30 (4H, d), 7.26-7.27 (1H, m), 6.98 (1H, s), 6.59 (1H, s), 3.890 (3H, s), 3.899 (3H, s), 3.51 (2H, s), 3.26 (2H, s), 2.87-2.90 (2H, d), 2.60-2.63 (2H, t), 2.27-2.29 (2H, d), 1.91-1.97 (2H, t), 1.81-1.83 (2H, t), 1.65-1.68 (2H, t), 1.28-1.49 (23H, m), 0.88-0.92 (3H, t).

Example 9

Compound 9: Preparation of Donepezil Hexadecanoate

The preparation process was the same as that of Example 2. Donepezil (30.0 g, 79.1 mmol) was reacted with hexadecanoic anhydride (58.7 g, 119 mmol), and subjected to post-processing. Insolubles were removed by filtration before crystallization. 38.0 g of the compound donepezil hexadecanoate was obtained (yield: 79.5%) with HPLC (area): 98.15%.

Mass spectrum (m/z): [M+H]$^+$=618.5.

$^1$H-NMR(CDCl3) δ:7.32-7.31 (4H, d), 7.25-7.27 (1H, m), 6.98 (1H, s), 6.59 (1H, s), 3.90 (3H, s), 3.89 (3H, s), 3.49 (2H, s), 3.26 (2H, s), 2.86-2.89 (2H, d), 2.60-2.63 (2H, t), 2.28-2.29 (2H, d), 1.90-1.96 (2H, t), 1.80-1.83 (2H, t), 1.65-1.68 (2H, t), 1.28-1.55 (29H, m), 0.88-0.92 (3H, t).

Example 10

Compound 10: Preparation of Donepezil Octadecanoate

The preparation process was the same as that of Example 2. Donepezil (2.00 g, 5.27 mmol) was reacted with octadecanoic anhydride (4.40 g, 8.00 mmol), and subjected to post-processing. Insolubles were removed by filtration before crystallization. 2.13 g of the compound donepezil octadecanoate was obtained (yield: 62.6%) with HPLC (area): 98.15%.

Mass spectrum (m/z): [M+H]$^+$=646.5.

$^1$H-NMR(CDCl3) δ:7.32-7.30 (4H, d), 7.25-7.27 (1H, m), 6.98 (1H, s), 6.59 (1H, s), 3.890 (3H, s), 3.898 (3H, s), 3.50 (2H, s), 3.26 (2H, s), 2.87-2.89 (2H, d), 2.60-2.63 (2H, t), 2.27-2.29 (2H, d), 1.91-1.96 (2H, t), 1.81-1.83 (2H, t), 1.66-1.68 (2H, t), 1.28-1.60 (31H, m), 0.88-0.92 (3H, t).

Example 11

Formulation:

| Component | Formulation amount |
| --- | --- |
| compound 4 | 100 mg |
| benzyl benzoate | 200 mg |
| benzyl alcohol | 100 mg |
| castor oil | 1 ml |

Preparation Process:

Compound 4, benzyl alcohol, and benzyl benzoate of respective formulation amounts were dissolved in castor oil. Stir until the substances were completely dissolved. 0.22 μm filter membrane was used for filter sterilization. Stopper and capto obtain oily preparations.

Example 12

Pharmacokinetic Properties of Compounds of the Present Invention Administered to Rats In the present embodiment, male SD rats (SPF grade), aged 9 months and weighing 180 to 220 g, were purchased from Shanghai Slack laboratory Animal Co., Ltd. Throughout the process of the experiment, give the rats free access to food and water.

Adopting grouping of random grouping design, the SD rats for experiments were grouped according to gender and body weight. They were divided into donepezil group, compound 1 group, compound 3 group, compound 4 group, and compound 6 group. Rats of each group were administered by intramuscular injection (i.m.) with the dose set at 90 mg/kg (based on donepezil). The samples were dissolved in oil solvent at a concentration of 90 mg/ml (based on donepezil).

Figure 2:
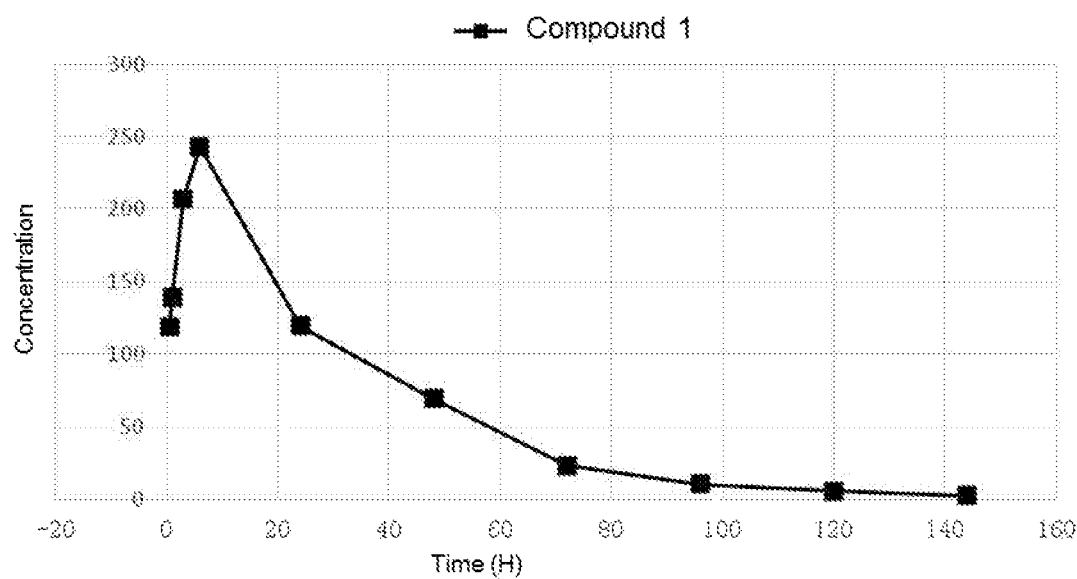
FIG. 2 shows the relationship between drug concentration in plasma and time in the group of rats administered with compound 1.
Figure 3:
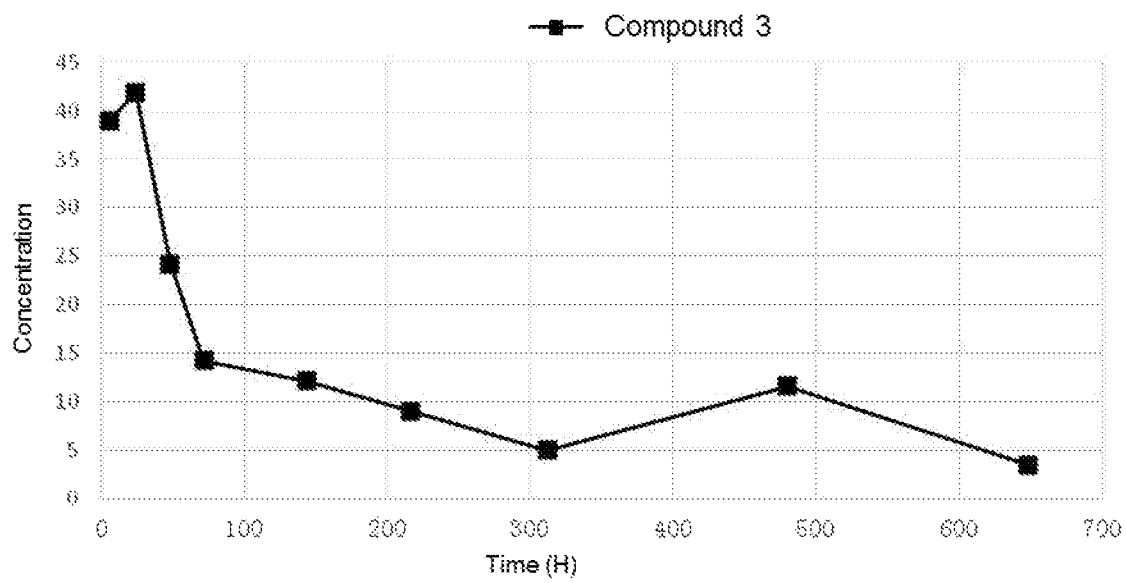
FIG. 3 shows the relationship between drug concentration in plasma and time in the group of rats administered with compound 3.
Figure 4:
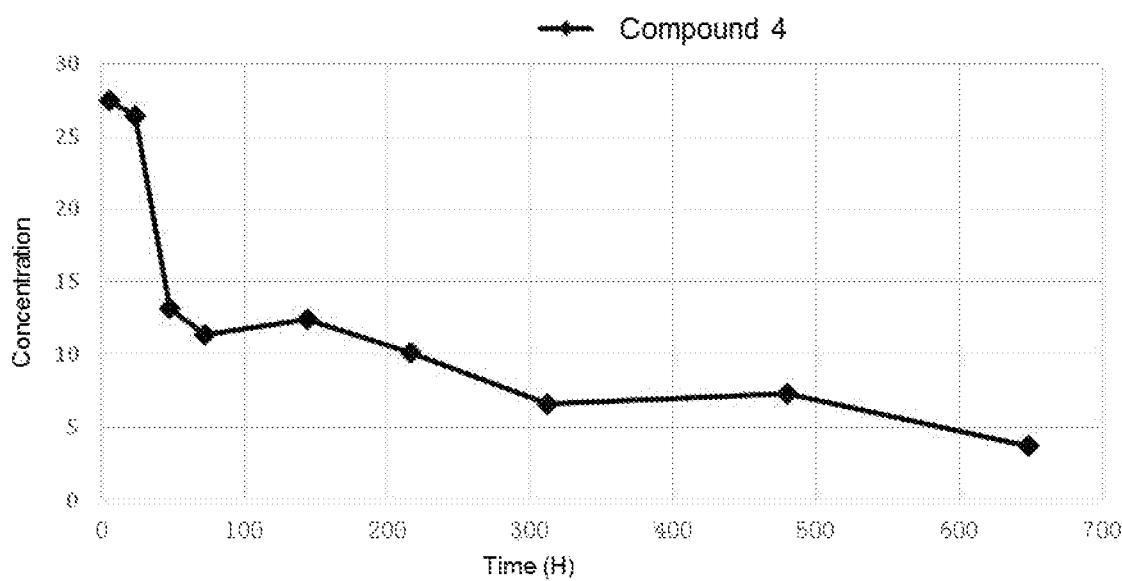
FIG. 4 shows the relationship between drug concentration in plasma and time in the group of rats administered with compound 4.
Figure 5:
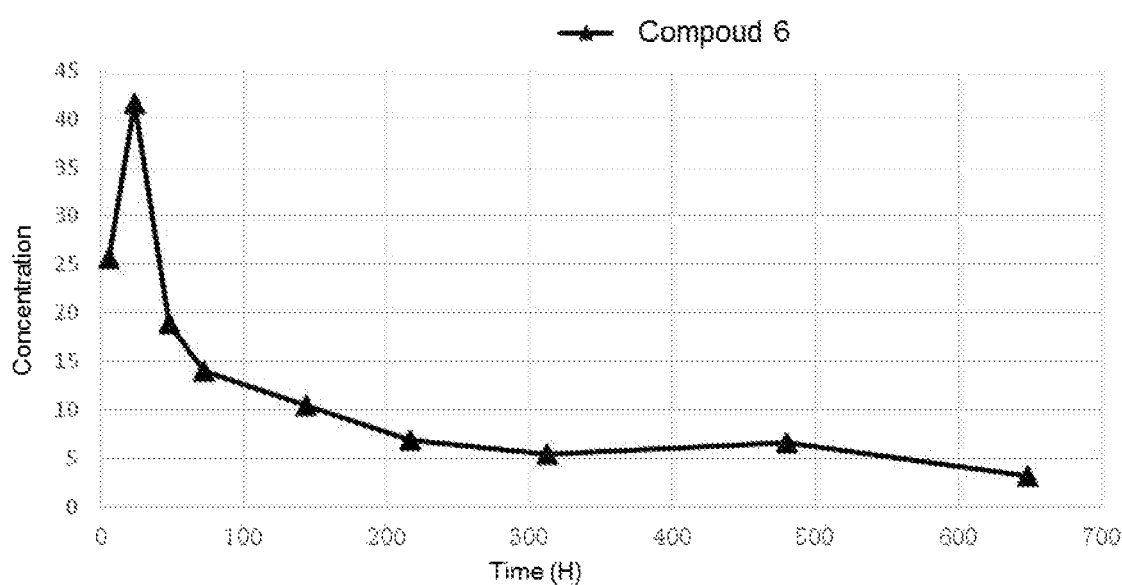
FIG. 5 shows the relationship between drug concentration in plasma and time in the group of rats administered with compound 6.

At 4 h, 8 h, 24 h (2 days), 3 days, 4 days, 5 days, 7 days, 9 days, 12 days after administration, 0.5 ml of venous blood was collected from ocular fundus venous plexuses and placed into a pre-labeled EDTA (4 mM) anticoagulated EP tube. The whole blood was collected and placed on ice, followed by centrifugation at 4° C., 8000 rpm and 5 min to collect plasma The plasma was transferred to a 96-well plate and stored at −20° C. until LC-MS/MS examination. Drug concentrations in EDTA (4 mM) anticoagulated plasma of SD rats were determined using LC/MS/MS (Agilent6460). Concentration v.s. time curves of each group are shown in FIGS. 1-5. Using WinNonlin 5.2 software, calculate respective relevant pharmacokinetic parameters of each group at each time point after administration according to statistical moment theory. See Table 1 for the details.

TABLE 1

|  | donepezil group | compound 1 group | compound 3 group | compound 4 group | compound 6 group |
|---|---|---|---|---|---|
| $T_{1/2}$, hr | 13.34 | 22.76 | 314.18 | 426.92 | 287.47 |
| $T_{max}$, hr | 0.67 | 6.00 | 18.00 | 18.00 | 24.00 |
| $C_{max}$, ng/ml | 361.10 | 243.17 | 44.11 | 30.80 | 41.60 |

$C_{max}$ and $T_{max}$ were represented in measured values.

$t_{1/2}$ was calculated by the formula $t_{1/2}=0.693/\lambda z$; $\lambda z$ is an end elimination rate constant derived from the logarithmic concentration—the straight part of the end of time curve, which can be derived from the slope of the logarithmic concentration—the straight part of the end of time curve.

Conclusion: From the above experimental results, it can be seen that the compounds of the present invention have the advantages of long half-life and avoiding rapid increase of plasma drug concentration.

The foregoing are only preferred embodiments of the present invention. It ought to be noted that several improvements and modifications may be made by those skilled in the art without departing from the principles of the present invention. These improvements and modifications should be regarded as the scope of protection by the present invention.

What is claimed is:

1. A compound of formula (I):

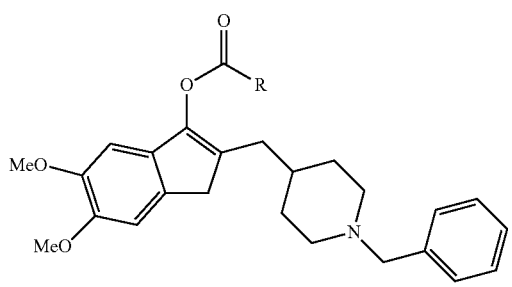

(I)

or a pharmaceutically acceptable salt thereof, wherein R is $C_6$ alkyl group.

2. The compound of claim 1 or a pharmaceutically acceptable salt thereof, wherein R is n-hexane.

3. A method of treating dementia in a patient, comprising:
administering to said patient a compound according to claim 1 or the pharmaceutically acceptable salt thereof.

4. A pharmaceutical composition, comprising a compound according to claim 1 or the pharmaceutically acceptable salt thereof, and a pharmaceutically acceptable excipient.

5. The pharmaceutical composition of claim 4, wherein the excipient is selected from one or more of castor oil, soybean oil, sesame oil, *arachis* oil, corn oil, cottonseed oil, or glycerides.

6. The pharmaceutical composition of claim 4, further comprising a hydrotropic agent, wherein the hydrotropic agent is selected from one or more of benzyl benzoate or alcohols.

7. The pharmaceutical composition according to claim 4, further comprising a pain relief agent, wherein the pain relief agent is benzyl alcohol.

8. The pharmaceutical composition of claim 5, wherein the excipient is castor oil.

9. The pharmaceutical composition of claim 6, wherein the hydrotropic agent is benzyl benzoate.

10. A method of treating dementia in a patient, comprising:
administering to said patient a pharmaceutical composition comprising a compound according to claim 1 or the pharmaceutically acceptable salt thereof; and a pharmaceutically acceptable excipient.

11. The method of claim 10, wherein the excipient comprises castor oil.

12. The method of claim 10, wherein the pharmaceutical composition further comprises a hydrotropic agent, wherein the hydrotropic agent is benzyl benzoate.

13. The method of claim 3, further comprising administering to said patient a pain relief agent, wherein the pain relief agent is benzyl alcohol.

14. The method of claim 10, further comprising administering to said patient a pain relief agent, wherein the pain relief agent is benzyl alcohol.

* * * * *